United States Patent
Ko et al.

(10) Patent No.: US 8,894,700 B2
(45) Date of Patent: Nov. 25, 2014

(54) ABDOMINAL AORTIC STENT

(71) Applicants: Po-Jen Ko, Taipei (TW); Ching-Yang Wu, New Taipei (TW); Yun-Hen Liu, Taoyuan County (TW); Hui-Ping Liu, Taipei (TW)

(72) Inventors: Po-Jen Ko, Taipei (TW); Ching-Yang Wu, New Taipei (TW); Yun-Hen Liu, Taoyuan County (TW); Hui-Ping Liu, Taipei (TW)

( * ) Notice: Subject to any disclaimer, the term of this patent is extended or adjusted under 35 U.S.C. 154(b) by 0 days.

(21) Appl. No.: 13/845,194

(22) Filed: Mar. 18, 2013

(65) Prior Publication Data

US 2013/0218258 A1    Aug. 22, 2013

Related U.S. Application Data

(63) Continuation-in-part of application No. 12/790,956, filed on May 31, 2010, now abandoned.

(51) Int. Cl.
*A61F 2/06* (2013.01)
*A61F 2/07* (2013.01)
*A61F 2/89* (2013.01)

(52) U.S. Cl.
CPC ... *A61F 2/06* (2013.01); *A61F 2/07* (2013.01); *A61F 2002/067* (2013.01); *A61F 2230/0034* (2013.01); *A61F 2/89* (2013.01)
USPC ....... 623/1.16; 623/1.12; 623/1.13; 623/1.31; 623/1.35

(58) Field of Classification Search
CPC .......... A61F 2002/065; A61F 2002/07; A61F 2230/0067
USPC ................................. 623/1.13, 1.35
See application file for complete search history.

(56) References Cited

U.S. PATENT DOCUMENTS

| | | | |
|---|---|---|---|
| 7,175,651 B2 | 2/2007 | Kerr | |
| 7,413,573 B2 * | 8/2008 | Hartley et al. | 623/1.13 |
| 2006/0161244 A1 | 7/2006 | Seguin | |
| 2007/0142896 A1 * | 6/2007 | Anderson et al. | 623/1.13 |
| 2007/0162109 A1 | 7/2007 | Davila et al. | |
| 2009/0287145 A1 | 11/2009 | Cragg et al. | |
| 2011/0130820 A1 * | 6/2011 | Cragg et al. | 623/1.11 |

* cited by examiner

*Primary Examiner* — Bruce E Snow
*Assistant Examiner* — Brian Dukert

(57) ABSTRACT

An abdominal aortic stent includes a first sub-stent and a second sub-stent each having a front end. The circumference of the front end of each sub-stent is half of the circumference of the abdominal aorta. When the circumference is gradually reduced to a rear end of each sub-stent, it has entered one side of the bilateral femoral arteries. The rear ends of the sub-stents with full circumference of the cross-sectional area of the femoral artery are included therein. The first and second sub-stents are coated with external removable membrane to compress the sub-stents to generate smaller circumferences. When the removable membrane has been removed, the sub-stents are fully extended to reconstruct the vascular flow path.

6 Claims, 8 Drawing Sheets

ABDOMINAL AORTIC STENT

BACKGROUND OF THE INVENTION

1. Field of the Invention

This invention relates to an abdominal aortic stent. More specifically, this invention relates to an abdominal aortic stent structure which can be easily implanted to reconstruct a vascular flow path.

2. Description of Related Art

The development of stents began since the late '90s to reconstruct normal vascular flow path by inserting stents to separate the aneurysm. It is called endovascular aneurysm repair (EVAR).

Conventionally, in clinical endovascular aneurysm repair practice, a metal wire is inserted from both sides of the femoral artery, and an appropriate stent size would be determined by surgery angiography according to the location, length and influential area of the aneurysm. The stent is then guided to an expected destination through the metal wire. After the membrane wrapped outside the stent is removed, the stent can fully extend to reconstruct a vascular flow path. According to clinical study, the endovascular aneurysm, comparing with conventional surgery, has the advantages of: (1) shorter operative time, (2) smaller amount of blood loss, and (3) shorter recovery time.

Referring to FIGS. 1 to 3, endovascular surgery could be performed via a small wound, which leads to less tissue damage. Also, endovascular surgery causes limited blood loss. Thus, the endovascular surgery has become a trend of modern vascular surgery. On the contrary, conventional abdominal aortic aneurysm surgery is a major vascular surgery, which would generate a 30 to 40 cm abdominal incision from the xiphoid (below the chest) to the top part of the pubic bone. The endovascular surgery can be performed by using a metal wire (1), a membrane (3) and a main stent (2). With the assistance of intra-operative fluoroscopy, the stent can be sent from both sides of the femoral artery into the dilatation position of the abdominal aorta. After the main stent (2) is well positioned, the membrane (3) will be pulled down to have the main stent (2) deploy within the abdominal aortic aneurysm, such that the blood can flow into the main stent (2). If the membrane (3) is continuously pulled down, the main stent (2) will be completely open. Likewise, to connect the main stent (2) to a sub-stent (5), the first step is to put another metal wire (4) through a branch opening (2a) of the main stent (2), and the sub-stent (5) can be guided along the metal wire (4) to an appropriate location. However, sometimes if the blood vessel of a patient has a larger angle, or the branch opening (2a) is hard to be located, it may be difficult to cannulate the metal wire (4) to the branch opening (2a) of the main stent (2), which may increase operation time and even lead to operation related complications.

Therefore, there remains a need for a new and improved stent structure to overcome the abovementioned issues to effectively implant the stent into the abdominal aorta to reconstruct a vascular flow path.

SUMMARY OF THE INVENTION

It is an object of the present invention to provide a stent structure to effectively implant the stent into the abdominal aorta to reconstruct a vascular flow path.

It is another object of the present invention to provide a stent structure with two sub-stents to shorten surgery time, reduce surgery-related complications and help the patient recover faster.

It is a further object of the present invention to apply a stent structure (having two sub-stents) in a renal artery, with a first sub-stent comprising a first metal net and a first membrane covering the first metal net, and with a second sub-stent comprising a second metal net and a second membrane covering the second metal net. There are three re-set round side holes which encircle with a metallic ring at a cephalic part of each stent. The metallic rings of these side holes were incorporated to metallic framework and are all covered with a membrane. Metal rings are set along on the first metal net and the second metal net near the front ends respectively with an angle of 120° to the periphery, and are set axially at an equal distance along the first and second metal nets.

A location to place small stents is found rapidly through the metal rings by rotating the first and second sub-stents under the X-ray. A first membrane and a second membrane are stabbed at the predetermined metal rings, and the small stents are linked to the predetermined metal rings and connected to the renal artery.

The present invention together with the above and other advantages may best be understood from the following detailed description of the embodiments of the invention illustrated in the drawings below.

DETAILED DESCRIPTION OF THE INVENTION

Figure 1:
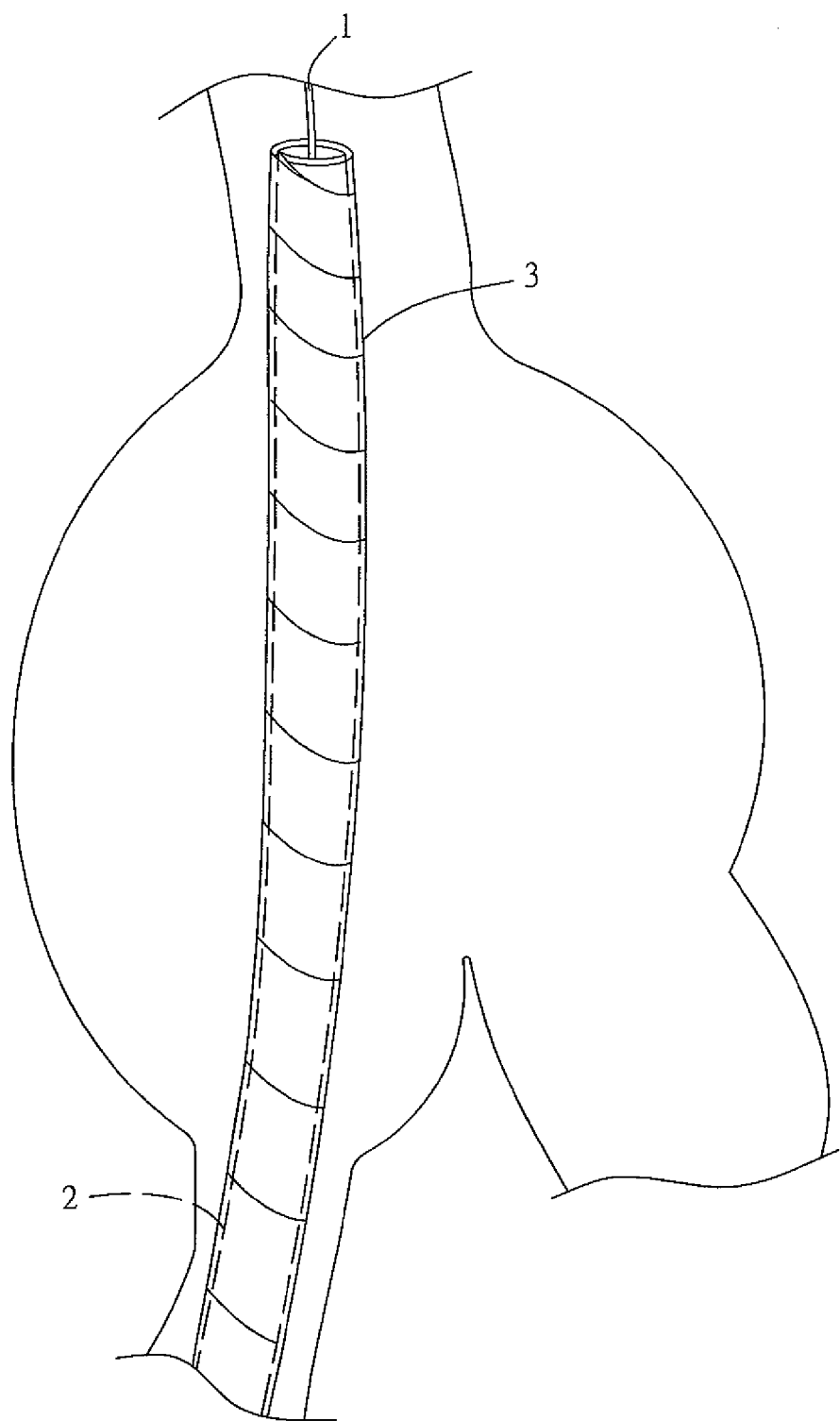
FIG. 1 illustrates a prior art, related to a conventional abdominal aortic stent.
Figure 2:
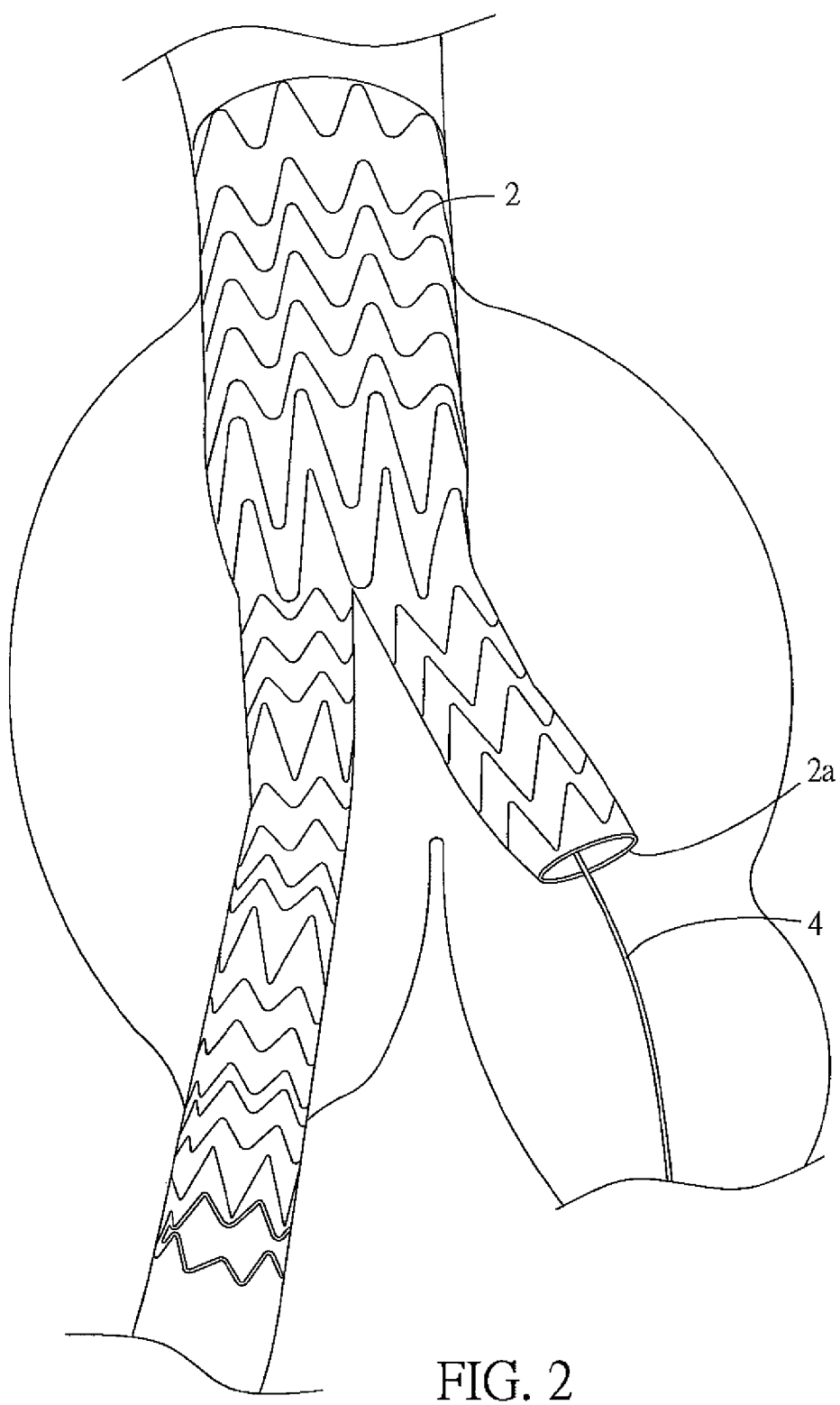
FIG. 2 illustrates a prior art, related to a conventional abdominal aortic stent with a branch opening.
Figure 3:
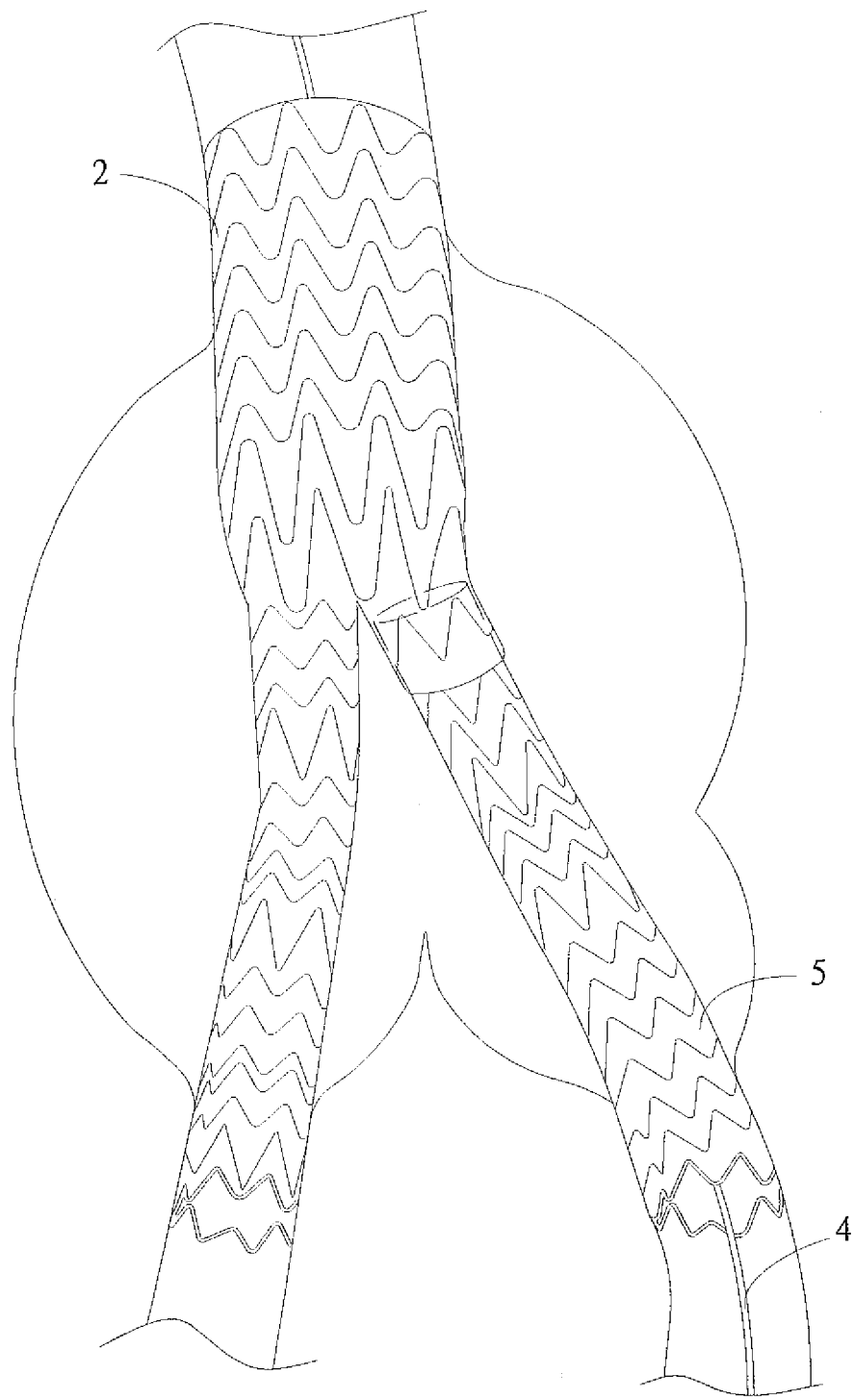
FIG. 3 illustrates a prior art, related to a conventional abdominal aortic stent connecting to a sub-stent.

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications which might be used in connection with the presently described invention. The publications listed or discussed above, below and throughout the text are provided solely for their disclosure.

This invention relates to an abdominal aortic stent. More specifically, this invention relates to an abdominal aortic stent structure with a shape which can be easily implanted to reconstruct a vascular flow path. Conventionally, most stents have a Y-shaped structure which is used for the reconstruction on one side of the iliac artery. Before being implanted, a metal wire has to be placed in a preserved path, and the stent can be guided to an appropriate location. However, sometimes if the blood vessel of a patient has a larger angle, it may be hard to cannulate the metal wire to the stent. Furthermore, it may be more difficult to cannulate another metal wire to a branch opening of the stent, which may increase surgery time and even lead to surgery-related complications.

The present invention provides a support structure (i.e. stent) for an abdominal aorta. The stent comprises a first and a second sub-stent, and a front portion of each sub-stent has a cross-sectional area which is half of the abdominal aorta. The cross-sectional area is gradually reduced, and at the very end of the sub-stent, it has entered one side of the bilateral femoral arteries. At the very end of the first and second sub-stents, the cross-sectional area of the sub-stents is entirely included in the femoral artery. Then, the first and second sub-stents can be fully extended within the vessel to reconstruct the vascular path after the external removable membrane coated on the sub-stents has been removed.

Unlike the conventional stents stated above, the abdominal aortic stent in the present invention comprises a first and second sub-stents, each of which constitutes half of the abdominal aortic stent. Therefore, the metal wires can be individually inserted into the arteries to guide the first and second sub-stents to predetermined locations. After the membrane thereon is removed, the stent can be fully extended within the vessel to reconstruct the vascular path, which makes the stent more convenient to use. Moreover, it can shorten operation time, reduce operation related complications and help the patient recover faster.

Figure 4:
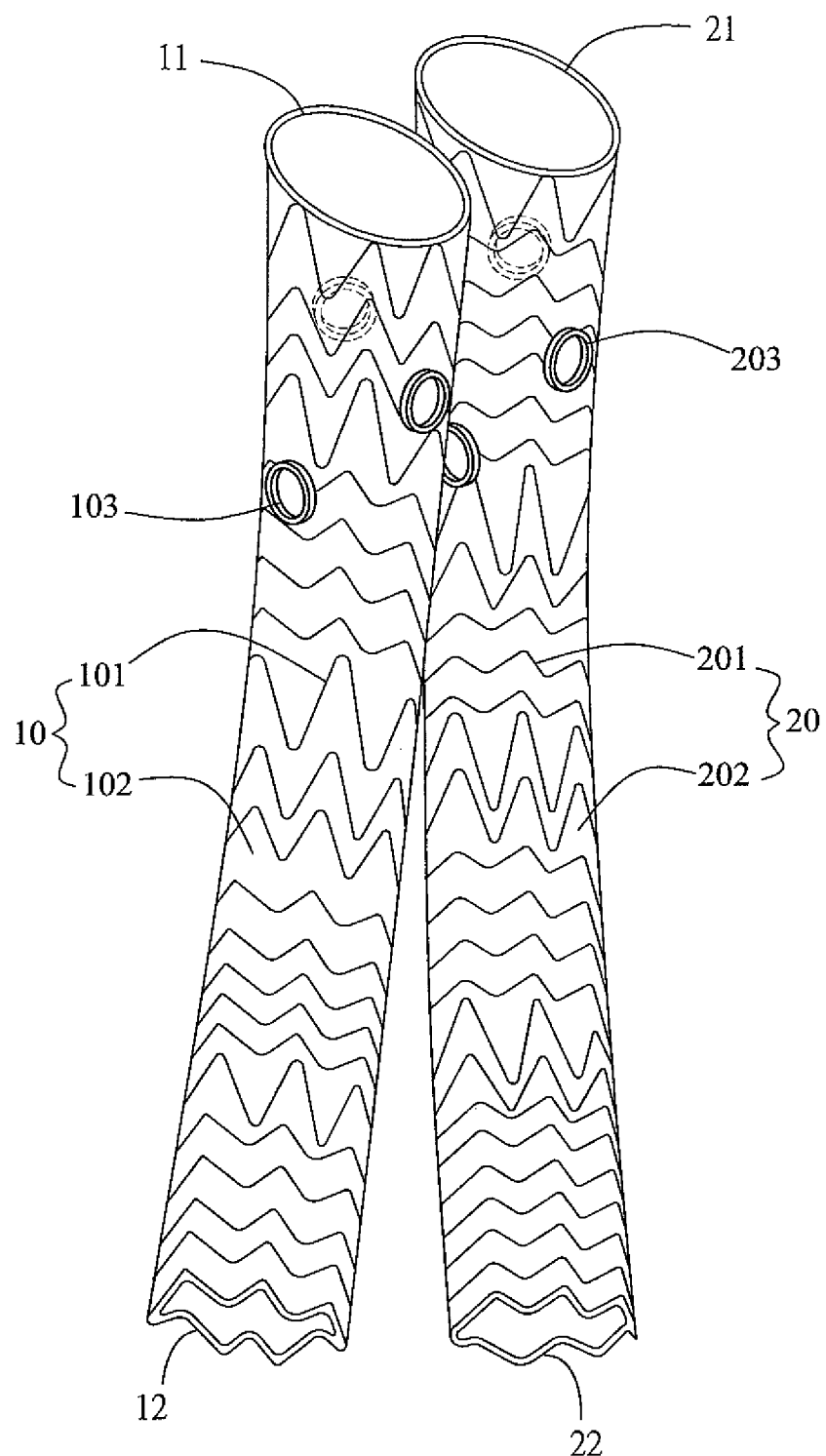
FIG. 4 illustrates a schematic view of one embodiment of the present invention.
Figures 5, 5A:
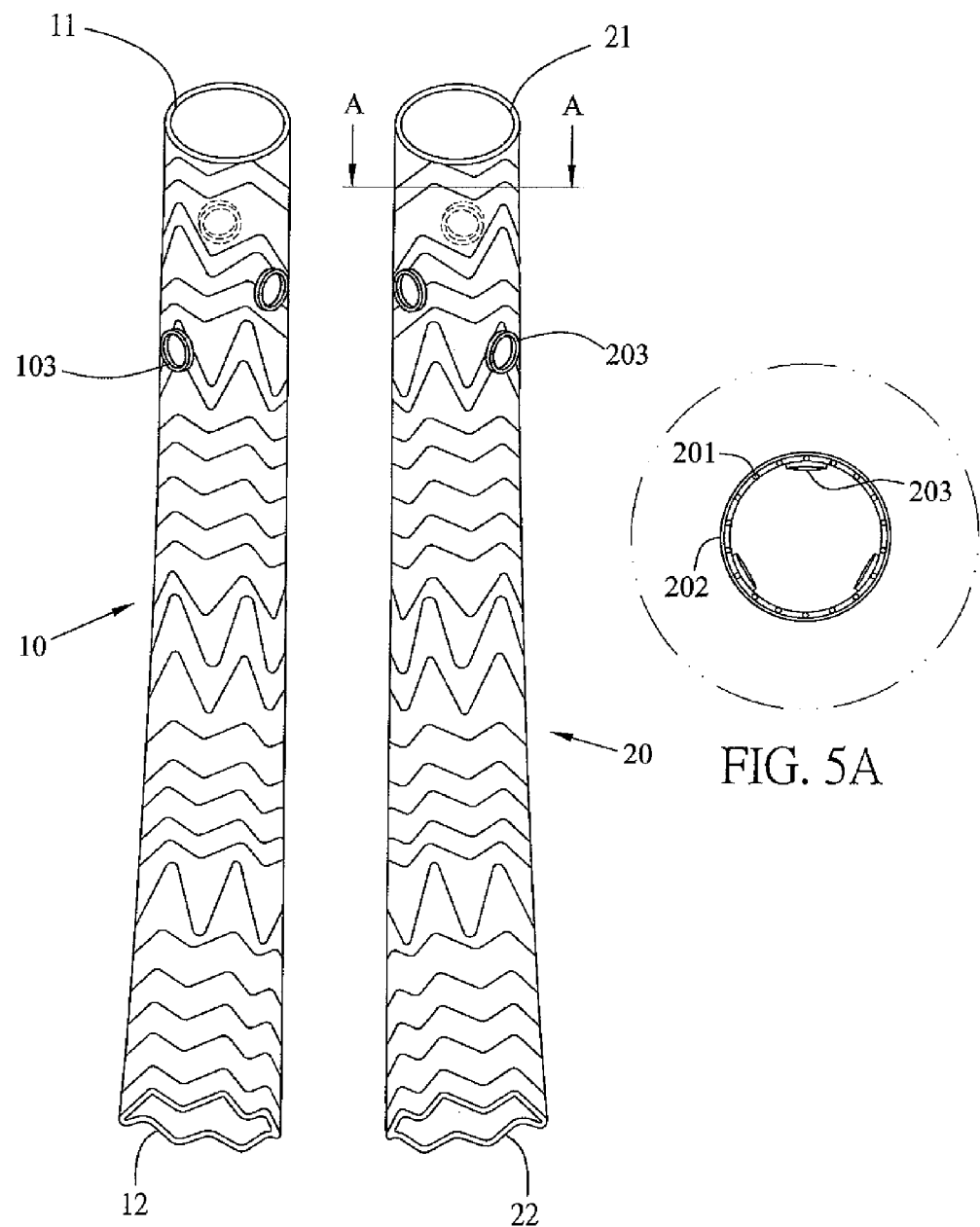
FIG. 5 illustrates a schematic view of the deployment of metal rings.
FIG. 5A illustrates another schematic view of the deployment of metal rings.
Figure 6:
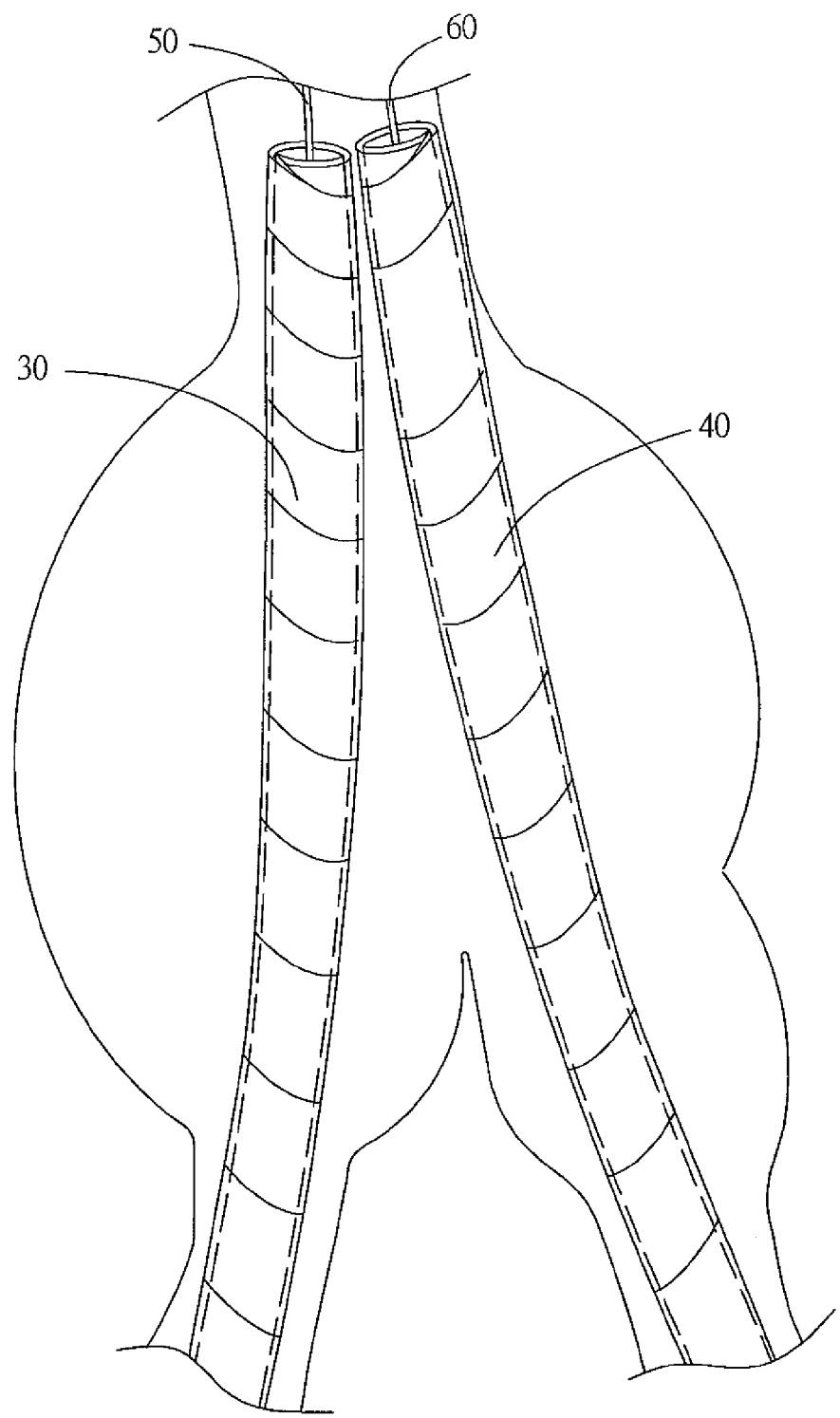
FIG. 6 illustrates a schematic view of metal wires put into the sub-stents of the present invention.
Figure 7:
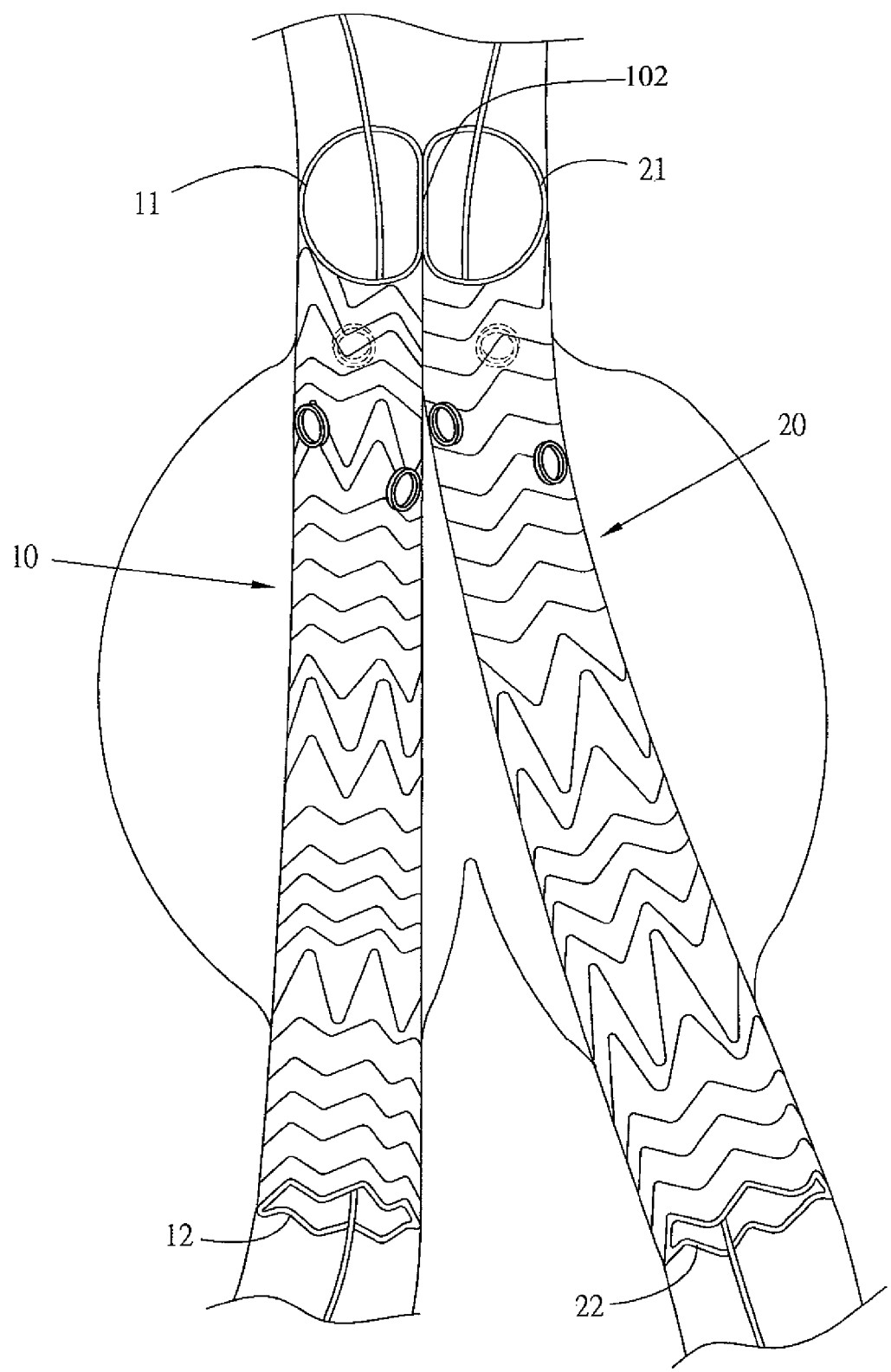
FIG. 7 illustrates a schematic view of sub-stents with metal wires penetrated through the sub-stents.
Figure 8:
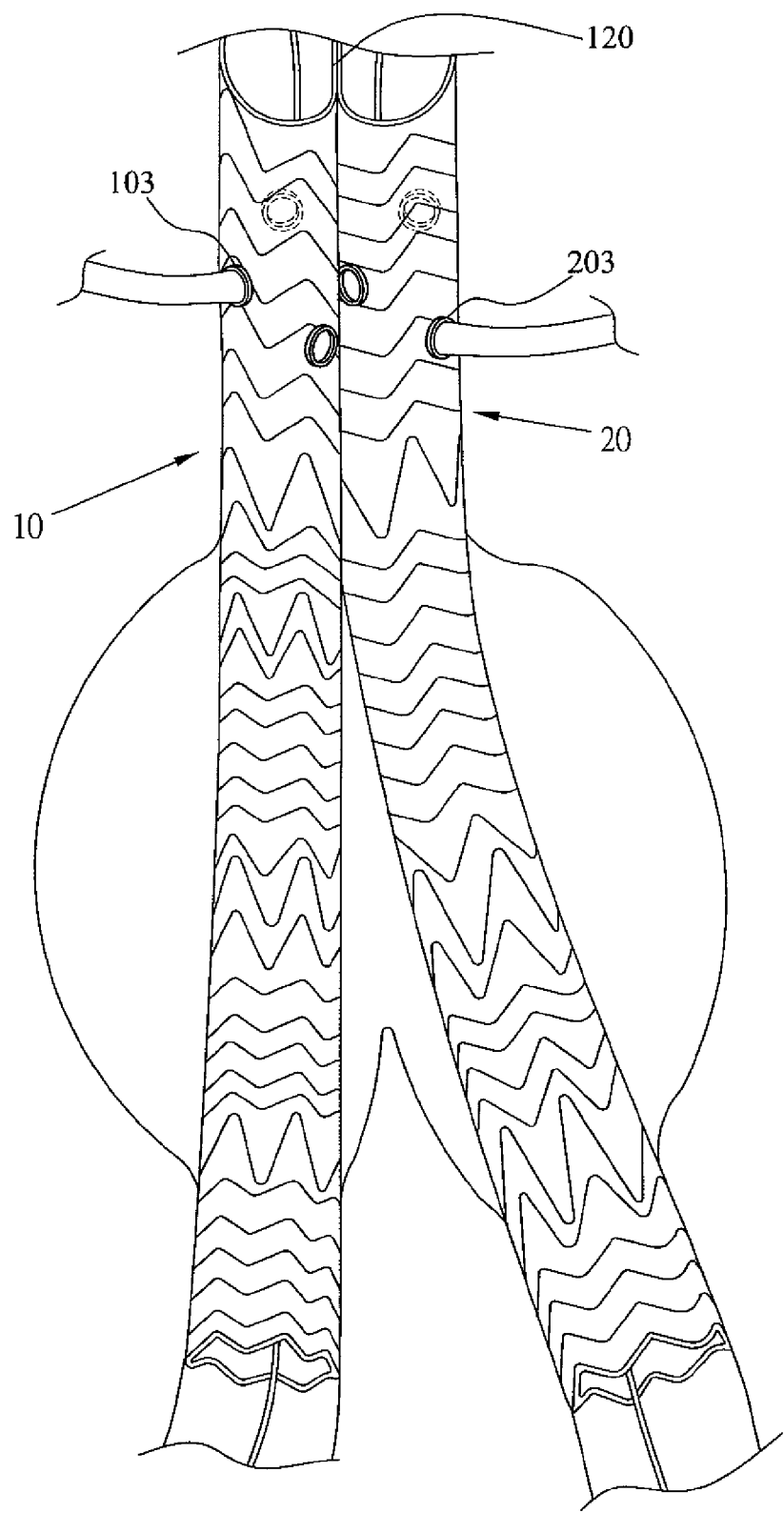
FIG. 8 illustrates a schematic view of a further embodiment of the present invention associated with a renal artery.

As seen in FIGS. 4 to 8, the present invention provides an abdominal aortic stent comprising two almost identical stents: a first sub-stent (10) and a second sub-stent (20), each having a front end (11) and (21), respectively. The circumference of the front ends (11, 21) of the first and second stents is half of the circumference of the abdominal aorta. When the circumference is gradually reduced to a rear end (12, 22) of each sub-stent (10, 20), it has entered one side of the bilateral femoral arteries. The rear ends (12, 22) of the first and second sub-stents (10, 20) with full circumference of the cross-sectional area of the femoral artery are included therein. The first sub-stent (10) comprises a first metal net (101) and a first membrane (102) covering the first metal net (101), and the second sub-stent (20) comprises a second metal net (201) and a second membrane (202) covering the second metal net (201). Metal rings (103, 203) are set on the first metal net (101) and the second metal net (201) near the front ends (11, 21) respectively with an angle of 120° to the periphery. The metal rings (103, 203) are set axially at an equal distance along the first and second metal nets (101, 201). The first and second sub-stents (10, 20) are coated with an external removable membrane (30, 40) to compress the first and second sub-stents (10, 20) to generate smaller circumferences. When the membrane (30, 40) has been removed, the first and second sub-stents (10, 20) can be fully extended within the vessel to reconstruct the vascular path.

In one embodiment, the front ends (11, 21) of the first and second sub-stents (10, 20) can be circular. After the membrane (30, 40) is removed simultaneously, the front ends (11, 21) resiliently lean against each other to form an interface (120) within the abdominal aortic vessel.

In one embodiment of the present invention, three metal rings (103, 203) are set on the first metal net (101) and the second metal net (201), respectively.

In one embodiment of the present invention, the metal rings (103, 203) are set axially at a distance of 0.5 cm along the first and second metal nets (101, 201).

In one embodiment of the present invention, the inner diameter of the metal rings (103, 203) is 0.5 cm.

In one embodiment of the present invention, the metal rings (103, 203) are combined with the first and second metal nets (101, 201) by welding.

In another embodiment of the present invention, the abdominal aortic stent comprises the first and second sub-stents (10, 20). Thus, the metal wires (50, 60) can be put through both sides of the femoral artery, and the first and second sub-stents (10, 20) can be guided along the metal wire (50, 60) to reach the predetermined position. When the membrane (30, 40) of the first and second sub-stents (10, 20) is removed, the first and second sub-stents (10, 20) will be fully extended within the vessel to reconstruct the vascular path, which makes the stent more convenient to use. Meanwhile, it can shorten operation time, reduce operation related complications and help the patient recover faster.

As to the abdominal aortic aneurysm (juxtarenal abdominal aortic aneurysm) which may affect the renal artery, longer sub-stents (10, 20) with the membrane may be selected. Furthermore, under the aid of an instrument, the location to place small stents can be found rapidly through the metal rings (103, 203) by rotating the first and second sub-stents (10, 20). The first and second membrane (102, 202) can be stabbed at the predetermined metal rings (103, 203), and the small stents can be linked to the predetermined metal rings (103, 203) and connected to the renal artery.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. An abdominal aortic stent comprising:
a first sub-stent having a front end and a rear end;
a second sub-stent having a front end and a rear end, with the second sub-stent being free of attachment with the first sub-stent, wherein the first and second sub-stents are coated with a stent membrane defining a vascular flow path, wherein an expanded circumference of each sub-stent is gradually tapered from the front end to the rear end, wherein the first sub-stent comprises a first metal net and a first membrane covering the first metal net, wherein the second sub-stent comprises a second metal net and a second membrane covering the second metal net, wherein metal rings are set on the first metal net and the second metal net near the front ends respectively and are spaced apart radially at an angle of 120° to a periphery of the first and second metal nets, wherein the metal rings are set axially at an equal distance along the first and second metal nets;
first and second small stents each adapted to be connected to a renal artery; and
an external removable membrane on each of the first and second sub-stents, with the external removable membrane compressing the first and second sub-stents to generate a smaller circumference smaller than the expanded circumference, with the smaller circumference being adapted to be half of a circumference of an artery, with the first and second sub-stents being fully extended to the expanded circumference with the external removable membrane removed and being free of attachment to each other, wherein the first and second small stents extended through stabbed openings in the stent membranes at predetermined metal rings in the first and second sub-stents and linked to the predetermined metal rings, and wherein a shape of the front end of each sub-stent is round.

2. The abdominal aortic stent of claim 1, wherein with the external removable membrane removed, the front ends resiliently lean against each other to form an interface.

3. The abdominal aortic stent of claim 1, wherein the metal rings are set axially at a distance of 0.5 cm along the first and second metal nets.

4. The abdominal aortic stent of claim 1, wherein the metal rings are combined with the first and second metal nets by welding.

5. The abdominal aortic stent of claim 1, wherein an inner diameter of the metal rings is 0.5 cm.

6. The abdominal aortic stent of claim 1, wherein three metal rings are set on the first metal net and the second metal net, respectively.

* * * * *